United States Patent [19]
Ehlert

[11] Patent Number: 5,948,968
[45] Date of Patent: Sep. 7, 1999

[54] OIL MIST GAUGE

[75] Inventor: Charles W. Ehlert, Katy, Tex.

[73] Assignee: Lubrication Systems Company of Texas, Inc., Houston, Tex.

[21] Appl. No.: 09/100,983

[22] Filed: Jun. 22, 1998

[51] Int. Cl.[6] .................................. G01N 9/00; F01M 1/00
[52] U.S. Cl. ............................ 73/30.04; 73/10; 184/6.4; 184/6.26
[58] Field of Search .............................. 73/10, 32 R, 434, 73/445, 447, 452, 453, 30.01, 30.04; 184/6.1, 6.4, 6.24, 6.26, 6.21; 340/506, 631

[56] References Cited

U.S. PATENT DOCUMENTS

| | | | |
|---|---|---|---|
| 3,587,079 | 6/1971 | Obergefell et al. | 250/218 |
| 3,939,944 | 2/1976 | Mitchell et al. | 184/6.26 |
| 4,527,661 | 7/1985 | Johnstone et al. | 184/6.4 |
| 5,125,480 | 6/1992 | Gregory et al. | 184/6.4 |
| 5,318,152 | 6/1994 | Ehlert | 184/6.4 |
| 5,718,744 | 2/1998 | Ehlert | 184/6.24 |

*Primary Examiner*—Hezron Williams
*Assistant Examiner*—Helen C. Kwok
*Attorney, Agent, or Firm*—Bill B. Berryhill

[57] ABSTRACT

An oil mist density gauge for determining the density of oil mist flowing through an oil mist lubrication system. The oil mist density gauge comprises: a gauge body having an oil mist inlet for connecting the density gauge to the oil mist lubrication system and an air outlet for venting air therefrom; a filter device carried by the gauge body and by which oil mist flowing therethrough is separated into oil and oil-free air; and a collection reservoir attached to the gauge body for collecting and measuring oil separated from the oil mist. An eductor device may be provided in the gauge body for drawing oil mist from the oil mist inlet and for introducing air and entrained oil mist into the filter device under a positive pressure.

14 Claims, 1 Drawing Sheet

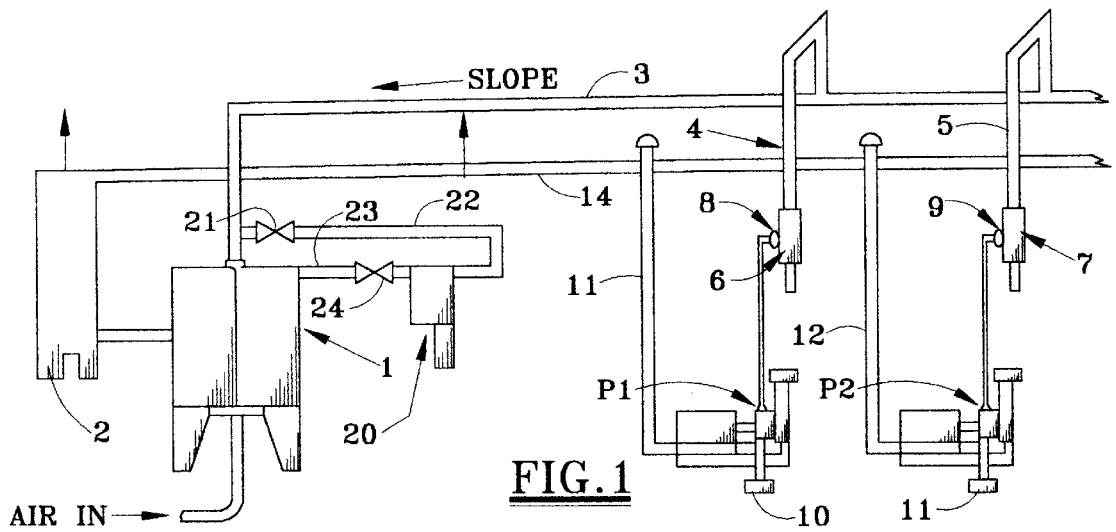
FIG.1
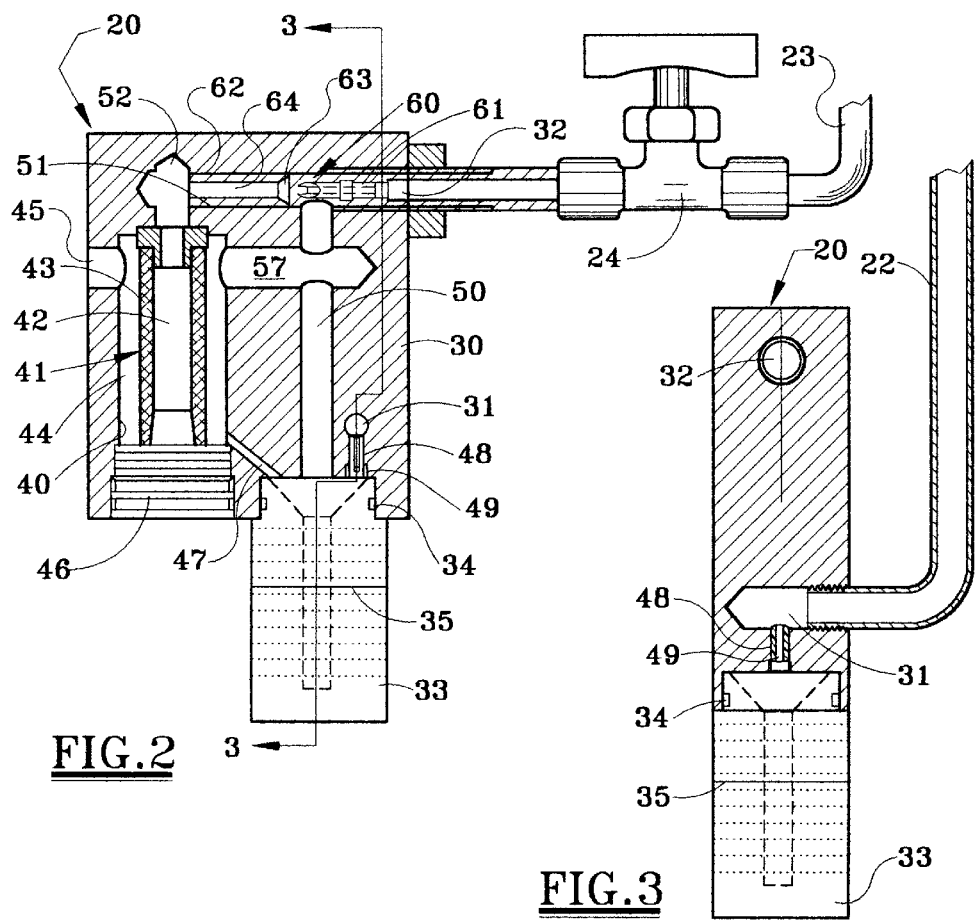
FIG.2
FIG.3

OIL MIST GAUGE

BACKGROUND OF THE INVENTION

1. Field of the Invention

The present invention pertains to lubrication systems for lubricating the bearings of bearing equipped items. More specifically, the present invention pertains to lubrication systems in which an oil mist is formed by combining air and oil and then distributed in the form of a dry oil mist to the bearings to be lubricated. More specifically, the present invention pertains to an oil mist gauge for determining the density of oil mist flowing through an oil mist lubrication system.

2. Description of the Prior Art

For many years bearings were lubricated by a "one shot" application of grease and/or oil to a grease or oil fitting with a grease gun or oil can. Although attempts were made to apply the grease or oil at periodic frequencies, many times too much oil and/or grease was used and, at other times, not enough oil and/or grease was provided for lubrication. For this reason, lubrication systems which apply the lubricant at timed periodic intervals or on a continuous basis were developed. U.S. Pat. No. 4,445,168 discloses a computer controlled lubrication system in which individual "shots" of lubricant are periodically delivered based on either a time cycle or a machine stroke cycle. U.S. Pat. No. 4,527,661 utilizes what is referred to in the industry as an "air-oil lubrication system" in which separate oil and air streams are brought to and combined by a mixing device, i.e. an atomizer, at a point immediately adjacent to the bearing being lubricated. These systems require two sets of piping (one for oil and one for air) and individual mixing devices at each point of lubrication.

In more recent years, oil mist lubrication systems have been developed to provide continuous, more effective lubrication to anti-friction bearings of rotating equipment such as centrifugal pumps, electric motors, speed turbines, gear boxes, blowers and fans. An oil mist lubrication system typically comprises an oil mist generator in which a compressed air stream, in turbulent flow, is combined with a liquid lubricant to create a fine mist of oil particles suspended in an air stream. These oil particles are typically one to five microns in diameter. The oil mist is transported through a piping system and delivered to the bearing housings of rotating equipment. The oil mist continuously lubricates the bearings of the equipment and maintains a slight positive pressure in the bearing housing to reduce contamination from outside sources. When oil mist is generated by such a system, the oil is atomized into very fine particles, typically one to five microns in diameter, so that the oil mist will remain stable and can be transferred relatively long distances with minimum wetting out on the walls of the pipe in which it is being conveyed. These fine particles, referred to as "dry oil mist", must be converted into larger particles, referred to as "wet oil mist", in order to wet out on the metal surfaces of the equipment bearings being lubricated. This is accomplished by passing the dry mist through a specially designed restriction orifice known as a "reclassifier". The reclassifier induces turbulence in the stream to combine small particles into larger ones before the mist (wet oil mist) enters the equipment bearing housing. These reclassifiers serve the additional purpose of metering the amount of lubricant to each bearing to avoid over or under lubrication. Selection of the correct reclassifier for each application point in the system is based upon an understanding of the exact bearing configuration for each piece of equipment to be lubricated. Such a system is described in U.S. Pat. No. 5,125,480.

U.S. Pat. No. 5,318,152 discloses an even more advanced oil mist lubrication system in which oil mist from an oil mist generator is distributed through a distribution assembly which includes one or more reclassifiers for converting the dry oil mist to a wet oil mist just prior to application to be bearing to be lubricated. This system also provides collection means into which excess oil and oil mist may flow and accumulate after lubrication of bearings. The excess oil mist and, in some cases, the excess oil collected may be returned for recycling and reuse. A demisting filter may be provided for separating the returned excess oil mist into oil and oil-free air, the oil accumulating for reuse and the oil-free air being vented to the atmosphere.

To assure that an oil mist lubrication system is supplying sufficient lubricating oil, the quantity of oil in the oil mist of an operating oil mist system must be determined. If the quantity of oil is too low, the bearings of the system may not be sufficiently lubricated. If the quantity of oil in the oil mist is too high, too much lubricating fluid will be wasted. A waste of oil, such as mineral oil, could be expensive and a waste of synthetic oil, typically more costly than mineral oil, could be very expensive. Thus, it is important to measure or monitor the density of oil in the oil mist of an oil mist system.

In prior procedures, the quantity of oil in the oil mist of an operating oil mist system (referred to in the industry as the mist density) have been difficult to carry out and do not yield good results. The procedure most commonly followed is a "consumption test". In such a test, oil usage over a set period of time is measured and based on the SCFM (system cubic feet per minute) of the system, as defined by totaling the flow of all reclassifiers, the mist density is supposedly measured. Such a test not only takes a long period of time, in most cases over 24 hours, but is not technically accurate. A typical consumption test procedure follows:

1. The consumption test involves measuring the change in the oil level as shown on the level gauge of a central oil mist generator reservoir.
2. The automatic oil fill option on the generator is turned off during the test which runs over a 24 hour period. Automated drain legs are also deactivated.
3. The change in level on the level gauge is converted to a volume measure by applying the known cross-sectional area of the generator reservoir to the level change, thus determining the amount of oil sent out of the unit over the duration of the test.
4. The input air volume of the system is assumed to be equal to the sum of the rated flow of all reclassifiers in the system.
5. The flow rate through each reclassifier is assumed to be the design value for a system operating at 20 inches of water column pressure; 501 ≃0.09 SCFM, 502 ≃0.18 SCFM, etc.
6. A physical count of the reclassifiers is made, a difficult and time consuming task on large mist systems.
7. The system is set to operate at 20 inches of water column pressure.
8. Mist density or oil/air ratio is then calculated by taking the cubic inches of oil sent out of the generator over the test period and dividing this figure by the presumed air consumption of the system.
9. The figure is normalized to an hourly rate so that the result is presented as "cubic inches of oil per hour per SCFM".

Such a procedure can be demonstrated as being obviously inaccurate by considering two mist systems which are the same (head size, flow rate, number of lubrication points, etc.) except that with one the mist header is sloped away from the generator while in the other the header is sloped toward the generator. Assume that in such a consumption test of both systems the reduction in oil level of the two generators was the same over the 24 hour test period. The test calculations as defined in the above procedure would then show that oil consumption and therefore, implied oil mist density, was the same for each system because the outputs of oil from each reservoir were identical. One can easily see, however, that the mist density of the two systems is not identical. The system with the header pipe sloped toward the generator must produce a much denser oil mist to achieve the same reduction in oil level in the reservoir since all of the oil mist coalescing in the header flows back to the generator reservoir. The system with the header pipe sloped away from the generator needs only to produce a much leaner oil mist to achieve the same measured consumption rate. The reason for this is the oil that coalesces in the header does not flow back to the generator reservoir. In measuring such a system in which the header pipe slopes back toward the generator, it may be assumed that 25% of the oil mist coalesced into liquid and collected in the header. This quantity of coalesced oil has a significant effect on measuring the oil consumption. In the assumed specific case of 25% return in a system where the header slopes toward the generator, the true mist density produced by the mist generating head must be 0.87 cubic inches of oil per hour per SCFM to achieve a net output of oil equal to 0.65, requiring a 33% richer and denser mist. Thus, measuring mist density by the traditional consumption test is inaccurate as the results are influenced by the header sloping.

It has been determined that mist flow to a bearing should be based on a target mist density of 0.65 cubic inches of oil per hour per SCFM. There is no need to be above this level and in fact many believe that the oil/air ratio can be less than 0.65. A more accurate method and apparatus for measuring oil mist density (oil/air ratio) is very much needed. A device for quantitatively and absolutely measuring the amount of oil in the oil mist stream, independent of header slope, is needed.

SUMMARY OF THE PRESENT INVENTION

In the present invention a stand alone oil mist density gauge for determining the density of oil mist flowing through an oil mist lubrication system is disclosed which is extremely accurate and independent of the slope of header piping. The mist density gauge of the present invention operates by stripping oil from a sample stream of oil mist. During operation, the oil is collected in a calibrated sight bottle and, after one hour of continuous operation, a direct reading of the air/oil ratio can be ascertained. All readings are measured as cubic inches of oil/hour/SCFM of flow.

The oil mist density gauge of the present invention provides a body having an oil mist inlet for connecting the oil mist density gauge to the oil mist lubrication system and an air outlet for venting air therefrom. A filter assembly is carried by the body for separating the oil mist flowing therethrough into oil and oil-free air. A collection reservoir or bottle is provided for collecting and measuring oil separated from the oil mist. The oil mist density gauge is provided with an air inlet and an eductor assembly by which air and entrained oil mist are introduced into the filter assembly under a positive pressure. The filter assembly comprises a chamber in which is disposed a filter element, the filter element being interposed between the oil mist inlet and the air outlet, for separating the oil mist into oil and oil-free air, the oil-free air for venting through the air outlet and the oil for draining from the chamber into the collection reservoir.

As stated, a mist system in a refinery or a petrochemical plant when generating oil mist at the target density of 0.65 cubic inches of oil per hour per SCFM will consume about one gallon of oil per day. If the oil mist generator is not properly adjustable, actual mist density could be double the target. At 1.3 cubic inches of oil per hour the oil consumption would be two gallons per day. If the client were using synthetic oil in the mist system at $14.00/gallon, proper monitoring could save over $5,000.00 per year simply by calibrating the system to the target of 0.65 level. If the cost of oil were only $4.00/gallon, typical of mineral oil, the yearly savings would still be more than $1,400.00 per year. The cost of monitoring and regulating oil with the oil gauge of the present system, at less than $400.00 per year, is thus easily justified with either type of lubricating fluid.

Furthermore, refineries and petrochemical plants are seeking ways to minimize stray mist not only to reduce lubricant consumption but to reduce air pollution. Many other objects and advantages of the invention will be apparent from reading the description of the invention in conjunction with the accompanying drawings.

BRIEF DESCRIPTION OF THE DRAWINGS

FIG. 1 is a schematic representation of an oil mist lubrication system, utilizing an oil mist density gauge, according to a preferred embodiment of the present invention, for determining the density of oil mist flowing therein;

FIG. 2 is an elevation view, partially in section, of an oil mist density gauge for use in determining the mist density of oil mist being distributed in an oil mist lubrication system such as the one illustrated in FIG. 1, according to a preferred embodiment of the invention; and FIG. 3 is a cross sectional view of the oil mist density gauge of FIG. 2, taken along lines 3—3 thereof.

DESCRIPTION OF A PREFERRED EMBODIMENT

Referring first to FIG. 1 there is a shown an oil mist is lubricating system for continuous lubrication of a plurality of bearings of one or more bearing equipped items. For illustration purposes, this system is shown being used to lubricate bearings of pumps and electric motors of electric motor driven pumps P1 and P2. Of course, the system could be used to lubricate many other numbers and types of items such as centrifugal pumps, steam turbines, gear boxes, blowers, fans, etc.

The oil mist lubrication system shown in FIG. 1 may comprise an oil mist generator generally depicted as being enclosed in a mist generator housing 1. For present purposes, it is sufficient to understand that the oil mist generator is provided with a source of compressed air (not shown). The source of oil may be an oil collection/supply vessel 2. The oil and air are properly heated, pressurized and flow regulated and brought together in the oil mist generator using a vortex or other type of mist head, creating an oil mist in which the oil is atomized into very fine particles which can be conveyed over long distances with a minimum wetting out on the walls of pipe through which it is being conveyed. These fine particles, are generally referred to as a "dry mist" in which the oil particles are typically one to five microns in diameter.

The dry oil mist generated in the oil mist generator then flows through a distribution header 3 and a plurality of pipe branches 4 and 5 to oil mist header manifolds 6 and 7. The supply header 3 and substantially horizontal portions of the mist distribution piping preferably slope downwardly in a direction toward the mist generator housing 1.

From the mist manifolds 6, 7, the oil mist flows through reclassifiers 8 and 9 which convert the small particles of oil in the dry oil mist supplied to the mist manifolds 6 and 7 to larger particles of oil (wet oil mist) for supplying wet oil mist to individual points of lubrication such as the bearings of the electric motor driven pumps P1, P2. The particular size and type of reclassifier 8, 9 is selected for the type of bearing to which the oil mist is to be supplied.

Some of the oil mist passing to points of lubrication may coalesce and be collected in collection containers 10 and 11. Excess oil mist, may be returned through risers 11 and 12 to a return header 14 which is connected to the oil collection/supply vessel 2. The oil collection/supply vessel 2 may be provided with a demister in which the returned oil mist is separated into oil and air. The oil is collected in the oil collection/supply vessel for return and reuse by the oil mist generator 1 and the oil-free air is vented to the atmosphere. In some cases, oil collected in the containers 10 and 11 may also be returned, by pumping or other means of transfer, to the oil collection/supply vessel 2 for reuse.

To measure and determine the density of oil mist being distributed to points of lubrication, an oil mist density gauge 20, according to the present invention, may be provided. Since a source of compressed air is available, the density gauge 20 is easily connected to a location very near the oil mist generator housing 1. In FIG. 1 the oil mist density gauge 20 is shown connected to the distribution header 3 through a valve 21 and conduit 22. Although shown to be connected adjacent the oil mist generator, the oil mist density gauge 20 may be utilized to verify the mist density at any point in the oil mist header system. For example, verification of target mist density to specific equipment (P1, P2) can be determined by connecting an oil mist density gauge to manifolds 4 and 5. The mist density gauge only needs a source of pressurized air. In FIG. 1, an air conduit 23 is shown connecting the gauge 20 to a source of pressurized air in the mist generator housing 1 through an air controlled valve 24.

Referring now also to FIGS. 2 and 3, the mist density gauge 20 will be described in greater detail. The oil mist density gauge 20 may comprise a gauge body 30 having an oil mist inlet 31 for connecting the gauge to the oil mist lubrication system through the conduit 22. It is also provided with an air inlet 32 which, as previously described is connected to a source of pressurized air through the conduit 23 and valve 24. In the preferred embodiment, the valve 24 is a needle valve utilized to adjust the volume of air from the source of pressurized air.

Connected to the gauge body 30 and depending therefrom is a collection bottle 33. The collection bottle 33 is preferably of a clear material having lines of calibration thereon, each line representing 0.1 cubic inches of oil per hour per SCFM. An intermediate line 35 is provided between the lines representing 0.6 and 0.7, indicating oil/air ratio of 0.65 cubic inches of oil/hour/SCFM of mist flow. The upper end of the collection bottle 33 is sealingly engaged by a seal 34 with a corresponding cylindrical recess in a lower portion of the gauge body 30 and is attached thereto in any suitable manner.

Carried within a cylindrical chamber 40 of the gauge body 30 is a filter assembly which includes a filter element 41 having a hollow core 42 surrounded by a wall of oil coalescing media 43. The outer surfaces of the filter element 41 and the walls of the chamber 40 define an annular space 44 which is vented to the atmosphere through an air vent 45. The chamber 40 may be provided with a closure member 46 which may be removed for installation and replacement of filter element 41. It will also be noted that an inclined drain passage 47 connects the bottom of the filter chamber 40 with the upper end of the collection bottle 33. The oil mist inlet 31 is also connected, through a small passage 48 in which is provided a condensing orifice 49, to the upper end of the collection bottle 33.

A fluid passage 50, vertically disposed above the collection bottle 33, intersects a horizontally disposed fluid passage 51 which is in fluid communication with the air inlet 32 and, through an outlet 52, with the hollow core 42 of the filter element 41. A bypass 57 also connects the first passage 50 with the annular space 44 surrounding the filter element 41.

The second fluid passage 51 carries an eductor assembly 60 which includes an air metering nozzle 61 and downstream thereof a reduced diameter flow nozzle 62. The flow nozzle 62 is provided with a converging entrance 63 and a reduced diameter cylindrical throat 64.

When oil mist flows into the oil mist inlet 31, it flows through the condensing orifice 49 of the passage 48. Some of the oil is condensed and drains into the collection bottle 33. The remaining oil mist flows upward through the passage 50 and into the second flow passage 51 or through the bypass passage 57 into the filter chamber 40. If pressurized air has been introduced into the air inlet 32, the air metering nozzle 61 increases the velocity of air to draw oil mist into the second flow passage 51 from the first flow passage 50. The flow nozzle 62 prevents reverse fluid flow through the second passage 51 and cooperates with the air metering nozzle 61 to introduce air and entrained oil mist into the core of the filter element 41 under positive pressure. The filter media 43 of the filter element 41 is pervious to air, allowing air in the air and entrained oil mist introduced into the filter assembly to pass through the filter element wall into the surrounding annular space 44 for venting through the air inlet 45. Oil coalescing and separated by the filter element 41 drains into the bottom of the chamber 40 and through the drain passage 47 into the collection bottle 33.

The flow rate of oil mist through the condensing orifice 49 is critical to proper operation of the oil mist density gauge. The orifice is designed to have a specific flow rate at a specified difference in pressure between its inlet and discharge sides. The design flow rate and pressure for the exemplary device is 0.16 SCFM ≃20 inches water. The inlet pressure of 20 inches water was selected because it is the most common oil mist system design operating pressure. Since the assumption is made that the separation of oil from air is 100% efficient, the volume of oil contained in 9.6 cubic feet of air (0.16 SCFM×60 minutes of operation) is what the device must quantify. In order to accomplish a direct method of measurement, the geometry of the collection bottle 33 bore is also critical. For this purpose, the bore preferably has a flat bottom and a specified diameter. To ensure correct readings during incremental adjustments and at test conclusion, the dimension between each line of calibration is equally important. Since the geometry of the oil collection bottle and the condensing orifice are fixed, if the pressure differential across the condensing orifice 49 (mist header pressure) is something other than 20 inches water, the flow rate changes. When this occurs the direct measurement of the mist density becomes skewed. This will require a mist pressure factoring table.

A very important function of the bypass passage 57 connecting the filter chamber 40 and the first vertical passage 50, is to maintain proper operating pressure differential across the condensing orifice 49. Air flow through the air metering nozzle 61 is varied by adjusting the air valve 24. As the valve is opened, air pressure, flow and velocity through the air metering nozzle increases. Without the bypass passage 57, if the air valve 24 is opened too much, excess air flow through the air metering nozzle 61 will create a negative pressure in the first air passage 50. A negative pressure in the first air passage 50 would be communicated to the discharge of the condensing orifice 49. The result is loss of calibration due to a differential pressure greater than 20 inches water across the condensing orifice 49. Also note that as the oil mist density gauge operates over time the coalescing filter element 42 becomes saturated with oil. As the oil saturation point is approached, the required pressure to maintain flow through the filer element 42 increases. Once saturated with oil, if the air flow is too low, insufficient pressure is developed at the discharge of the reduced diameter cylindrical throat 64 being communicated to the core of the coalescing filter element 42. Without the bypass passage 57 a positive pressure results in the first vertical passage 50 and is communicated to the discharge of the condensing orifice 49. The result of this operating condition is loss of calibration due to a differential pressure less than 20 inches water across the condensing orifice. A possible reverse flow condition through the condensing orifice occurs once the pressure in the first passage becomes greater than 20 inches water. The bypass passage 57 provides an atmospheric reference to the condensing orifice discharge. If the air supply to the air metering nozzle 61 is low, the pressure that results is relieved through the bypass passage, around the filter element 42 and out the discharge port 45 to atmosphere. This condition is noted during start-up by mist being visible as it escapes with the vented air. The operation of the oil mist density gauge is contingent upon the specified quantity of mist (9.6 cubic feet) being pushed through the coalescing filter 42 after one hour of operation. The addition of a small quantity of clean air does not affect its operation as long as the maximum flow rating for the coalescing filter element is not exceeded. Operation of the oil mist density gauge requires opening the air needle valve just until visible mist discharging from the vent connection ceases. Having sufficient pressure to pass through the filter element 42 and the differential pressure across the condensing orifice 49 is not affected. Without the bypass passage 57, adjustment to an operating atmospheric reference to the condensing orifice discharge would be virtually impossible.

In operation, the mist density gauge 20 is positioned, as shown in FIG. 1, so that the mist inlet connection 31 is lower than the connection point on the header 3. The connection conduit 22 should slope from the header connection to the gauge 20 without low points or pockets which would collect oil or restrict flow.

The air needle valve 24 is initially closed and connected to the air supply through the air supply line 23. With the air supply valve 24 closed and the oil mist system operating, stray mist will flow into the gauge body 30 through first passage 50 and bypass 57 into the chamber 40 and will escape through the air vent 45. The needle valve 24 should then be slowly opened until there are no visible signs of stray mist escaping from the air vent 45. It may be helpful to cup one hand over the vent hole 45 so that escaping mist is slowed down. This will also usually make it easier to detect the escaping mist. In addition, viewing the mist against a dark background will make it easier to see.

The oil mist density gauge will be operated until oil starts to collect in the oil collection sight bottle 33. If the gauge is being used for the first time, or if a new filter has been installed, the gauge should be operated until the filter element is saturated with oil. To verify that the filter has been saturated, the oil collection bottle 33 may be removed by grasping it and pulling it down to remove it from the gauge body. Saturation has occurred when oil can be seen dripping from the drain port 47.

Prior to taking measurements, the oil collection bottle 33 should be cleaned. Any oil therein should be wiped from the bottle. This could be done by inserting a paper towel into the bore of the bottle and twisting it in a direction to wipe out all oil therein. No solvents or paint thinners should be utilized in cleaning the bottle as this may cause the bottle of certain materials to be discolored or clouded so that the oil level therein would become difficult to observe.

After cleaning, the collection bottle 33 should be inserted into the gauge body 30. It is held in place by an interference fit between the O-ring 34 and the monitor body 30. The bottle can simply be pushed up into the cylindrical recess until the O-ring is compressed in the recess.

The pressure of the oil system and the mist header 3 should be set at 20 inches of water. While the oil mist system is operating, the air vent 45 should be checked for stray mist. If stray mist can be seen, the needle valve 24 should be further opened until there are no visible signs of stray mist escaping from the air vent 45. Again it may be helpful to cup one hand over the vent hole so that the escaping mist is slowed down or viewing the mist against a dark background to make it easier to see.

The mist density gauge is designed to give a direct reading of the oil/air ratio after exactly one hour of operation at a mist pressure of 20 inches of water. If the system operates at a mist header pressure other than 20 inches of water the direct reading option at the conclusion of the test must be factored to obtain a correct reading. A mist pressuring factor table could be utilized for this purpose.

After one hour of operation, the oil level and the oil collection sight glass may be viewed. As indicated, each line of the site glass represents 0.1 cubic inches of oil per hour per SCFM. There is an intermediate line 35 between the sixth and seventh line which represents the target oil/air ratio of 0.65 cubic inches of oil/hour/SCFM of mist flow.

When oil mist density is properly set at 0.65, while operating, the bottle should fill at a rate of approximately one line every ten minutes. By observing as oil fills the bottle, incremental adjustments can be made early in the test without waiting a full hour between mist head adjustments. Once the mist head has been adjusted to an output that appears to be acceptable, the oil consumption may be verified as described above. At the conclusion of testing, all oil may be drained from the collection bottle and wiped clean and if desired, the oil mist gauge may be removed and stored for future test.

Thus, the present invention provides a stand alone oil mist density gauge for determining and controlling oil/air density in a much more effective and accurate manner than the prior art. The cost of monitoring is easily offset by savings in lubricating fluids by preventing over-lubrication. The method utilized with the oil mist gauge of the present invention is quickly and accurately performed.

Although a single embodiment of the invention has been described herein, many alternate embodiments may be envisioned by those skilled in the art. Accordingly, it is intended that the scope of the invention be limited only by the claims which follow.

I claim:

1. An oil mist density gauge for determining the density of oil mist flowing through an oil mist lubrication system, said oil mist density gauge comprising:
   a gauge body having an oil mist inlet for connecting said density gauge to said oil mist lubrication system and an air outlet for venting air therefrom;
   oil and air filtering means carried by said gauge body and by which oil mist flowing therethrough is separated into oil and oil-free air; and
   oil collection means attached to said gauge body for collecting and measuring oil separated from said oil mist;
   said oil mist density gauge being further characterized by one or more fluid passages through said gauge body for flow of oil mist from said oil mist inlet to said filtering means, an air inlet being connected with said one or more fluid passages downstream of said oil mist inlet to provide pressurized air for entrainment of said oil mist therewith to said filtering means.

2. An oil mist density gauge as set forth in claim 1 including eductor means carried within one of said one or more flow passages through which air from said air inlet may flow for drawing said oil mist from said oil mist inlet and for introducing said air and entrained oil mist into said filtering means under a positive pressure.

3. An oil mist density gauge as set forth in claim 2 in which said eductor means comprises an air metering nozzle and, downstream thereof, a reduced diameter flow nozzle, said air metering nozzle being for receiving and metering air from said air inlet and for increasing the velocity of said air to draw said oil mist thereinto, said flow nozzle preventing reverse fluid flow and cooperating with said air metering nozzle for said introduction of said air and entrained oil mist into said filtering means under positive pressure.

4. An oil mist density gauge as set forth in claim 3 in which said flow nozzle comprises a converging entrance and a reduced diameter cylindrical throat.

5. An oil mist density gauge as set forth in claim 1 including a bypass passage providing fluid communication between said oil mist inlet and said filtering means downstream of said oil mist inlet but prior to introduction of pressurized air from said air inlet.

6. An oil mist density gauge as set forth in claim 1 in which said filtering means comprises a chamber in which is disposed a tubular filter element formed by a hollow core surrounded by a wall of oil coalescing filter media, said filter media being pervious to air, allowing air in said air and said entrained oil mist when introduced into said hollow core of said filter element to pass through said filter element wall into said surrounding chamber for venting through said air outlet.

7. An oil mist density gauge as set forth in claim 6 including a drain passage connecting said chamber to said collection means and through which oil separated from air by said filtering means may drain into said collection means for said collecting and measuring thereof.

8. An oil mist density gauge as set forth in claim 1 in which said filtering means comprises a chamber in which is disposed a filter element, said filter element being interposed between said oil mist inlet and said air outlet, for separating said oil mist into oil and oil-free air, said oil-free air for venting through said air outlet, said oil for draining from said chamber into said collection means.

9. An oil mist density gauge as set forth in claim 8 in which said oil mist inlet is provided with orifice means by which some of the oil in said oil mist is condensed for draining into said collection means, said oil mist inlet being in fluid communication with said collection means and said one or more flow passages through which the remaining oil mist may flow into said filtering means.

10. An oil mist density gauge as set forth in claim 9 including eductor means carried in one of said one or more passages and through which air may be introduced from a source of pressurized air, providing a draft for drawing said oil mist through said one or more passages and providing a positive pressure for forcing said air and said oil mist drawn therewith through said filtering means.

11. An oil mist density gauge as set forth in claim 9 including a bypass passage providing fluid communication between said filtering means chamber and said one or more flow passages.

12. An oil mist density gauge as set forth in claim 1 including a drain passage connecting said filter means to said collection means and through which oil separated from air by said filtering means may drain into said collection means for said collecting and measuring thereof.

13. An oil mist density gauge as set forth in claim 12 in which said oil mist inlet is provided with orifice means by which some of the oil in said oil mist is condensed for draining into said collection means for said collecting and measuring thereof without passing through said filtering means.

14. An oil mist density gauge as set forth in claim 12 in which said collection means comprises a calibrated container having an upper end of which is in fluid communication with said drain passage for said collecting and measuring of said oil separated from said oil mist by said filtering means.

* * * * *